(12) United States Patent
Lanzendörfer et al.

(10) Patent No.: US 7,052,716 B1
(45) Date of Patent: May 30, 2006

(54) COSMETIC AND DERMATOLOGICAL PREPARATIONS COMPRISING AN EFFECTIVE CONTENT OF BILE ACIDS, THEIR SALTS AND/OR THEIR DERIVATIVES

(75) Inventors: Ghita Lanzendörfer, Hamburg (DE); Volker Schreiner, Hamburg (DE)

(73) Assignee: Beiersdorf AG, Hamburg (DE)

( * ) Notice: Subject to any disclaimer, the term of this patent is extended or adjusted under 35 U.S.C. 154(b) by 488 days.

(21) Appl. No.: 09/744,506

(22) PCT Filed: Jul. 20, 1999

(86) PCT No.: PCT/EP99/05157

§ 371 (c)(1),
(2), (4) Date: Jan. 24, 2001

(87) PCT Pub. No.: WO00/07557

PCT Pub. Date: Feb. 17, 2000

(30) Foreign Application Priority Data

Aug. 1, 1998 (DE) ................................ 198 34 814

(51) Int. Cl.
*A61K 9/127* (2006.01)
*A61K 6/00* (2006.01)

(52) U.S. Cl. ............... 424/450; 424/401; 424/492; 424/494; 424/496; 424/78.02; 514/589; 514/766

(58) Field of Classification Search ............. 424/401, 424/490, 492, 494, 496, 78.02, 78.03, 450; 514/559, 766, 589
See application file for complete search history.

(56) References Cited

U.S. PATENT DOCUMENTS

| | | | |
|---|---|---|---|
| 4,115,313 A | | 9/1978 | Lyon et al. ............... 252/309 |
| 4,185,099 A | * | 1/1980 | Sorbini .................... 424/238 |
| 4,664,910 A | * | 5/1987 | Caserio et al. ............. 424/70 |
| 5,002,761 A | * | 3/1991 | Mueller et al. ............. 424/70 |
| 5,100,662 A | * | 3/1992 | Bolcsak et al. ............. 424/88 |
| 5,376,646 A | * | 12/1994 | Pittrof et al. .............. 514/78 |
| 5,747,066 A | * | 5/1998 | Pittrof et al. ............. 424/450 |
| 5,750,104 A | * | 5/1998 | Sipos .................... 424/94.21 |
| 6,066,352 A | * | 5/2000 | Ogasawara et al. ....... 426/549 |
| 6,251,428 B1 | * | 6/2001 | Yoo ...................... 424/455 |
| 6,267,985 B1 | * | 7/2001 | Chen et al. .............. 424/451 |

FOREIGN PATENT DOCUMENTS

| | | |
|---|---|---|
| DE | 195 22 694 A1 | 6/1995 |
| EP | 0 058 000 A2 | 1/1982 |
| EP | 0 329 312 A2 | 2/1989 |
| EP | 0 439 042 A1 | 1/1991 |
| FR | 2 375 859 | 1/1978 |
| FR | 2 551 991 A1 | 9/1983 |
| FR | 2 751 534 A1 | 1/1997 |
| JP | 03058918 * | 3/1991 |
| JP | 10120579 * | 5/1998 |

OTHER PUBLICATIONS

Patent Abstracts of Japan 03058918; Mar. 14, 1991, Koog Honpok:KK.
Derwint Abstract JP 10 120561 A (Pola Chem Ind. Inc.), AN 1998-328381, Week 199820.

* cited by examiner

*Primary Examiner*—Sreeni Padmanabhan
*Assistant Examiner*—Gina C. Yu
(74) *Attorney, Agent, or Firm*—Greenblum & Bernstein, P.L.C.

(57) ABSTRACT

Cosmetic and dermatological preparations having an effective content of bile acids, their salts and/or their derivatives, it being possible for said active ingredients to be present either individually or as a mixture.

7 Claims, No Drawings

COSMETIC AND DERMATOLOGICAL PREPARATIONS COMPRISING AN EFFECTIVE CONTENT OF BILE ACIDS, THEIR SALTS AND/OR THEIR DERIVATIVES

The present invention relates to cosmetic and dermatological preparations having an effective content of bile acids, their salts and/or their derivatives, and to the use thereof for strengthening the barrier function of the skin.

The skin is the largest human organ. Amongst its many functions (for example for temperature regulation and as a sensory organ) the barrier function, which prevents the skin (and thus ultimately the entire organism) from drying out, is probably the most important. At the same time, the skin acts as a protective device against the penetration and absorption of external substances. This barrier function is effected by the epidermis which, as the outermost layer, forms the actual protective sheath against the environment. Being about one tenth of the total thickness, it is also the thinnest layer of the skin.

The epidermis is a stratified tissue in which the outer layer, the horny layer (Stratum corium), is the part which is of significance for the barrier function. Being in contact with the environment, it is worn away and therefore finds itself in a continuous process of renewal, where, on the outside, fine flakes are continuously shed and, on the inside, keratinized cell and lipid material is subsequently produced.

The Elias skin model, which is currently recognized in the specialist field (P. M. Elias, *Structure and Function of the Stratum Corneum Permeability Barrier, Drug Dev. Res.* 13, 1988, 97–105), describes the horny layer as a two-component system, similar to a brick wall (bricks and mortar model). In this model, the horny cells (corneocytes) correspond to the bricks, and the lipid membrane, which is of complex composition, in the intercellular spaces corresponds to the mortar. This system essentially represents a physical barrier to hydrophilic substances, but, because of its narrow and multilayered structure, can equally, however, also be passed by lipophilic substances only with difficulty. The particular structure of the horny layer on the one hand protects the skin and on the other hand stabilizes its own flexibility by binding a defined amount of water.

Mechanical stresses, such as, for example, compressive forces, impacts or shear forces, can also be intercepted to a surprising degree by the horny layer alone or in conjunction with the deeper layers of the skin. Relatively large compressive forces, torsional forces or shear forces are transmitted to deeper layers of the skin via the meshing of the epidermis with the corium.

The regulation of the water and moisture content is one of the most important functions of the epidermal lipid membrane. However, it not only has a barrier effect against external chemical and physical influences, but also contributes to the holding together of the horny layer.

The lipids of the horny layer essentially consist of ceramides, free fatty acids, cholesterol and cholesterol sulfate and are distributed over the entire horny layer. The composition of these lipids is of decisive importance for the intact function of the epidermal barrier and thus for the water impermeability of the skin.

Even cleansing the skin using a simple waterbath—without the addition of surfactants—initially causes the horny layer of the skin to swell. The degree of this swelling depends inter alia on the bathing time and temperature. At the same time, water-soluble substances are washed off or out, such as e.g. water-soluble constituents of dirt, but also substances endogenous to the skin which are responsible for the water-binding capacity of the horny layer. In addition, as a result of surface-active substances which are endogenous to the skin, fats in the skin are also dissolved and washed out to a certain degree. After initial swelling, this causes a subsequent drying-out of the skin, which may be further considerably intensified by washing-active additives.

In healthy skin, these processes are generally of no consequence since the protective mechanisms of the skin are able to readily compensate for such slight disturbances to the upper layers of the skin. However, even in the case of nonpathological deviations from the norm, e.g. as a result of wear damage or irritations caused by the environment, photodamage, aging skin etc., the protective mechanism on the surface of the skin is impaired.

In aged skin, for example, regenerative renewal takes place at a slower rate, where, in particular, the water-binding capacity of the horny layer decreases. The skin thus becomes inflexible, dry and chapped ("physiologically" dry skin). Barrier damage is the result. The skin becomes susceptible to negative environmental effects, such as the invasion of microorganisms, toxins and allergens. As a consequence, toxic or allergic skin reactions may even result.

In the case of pathologically dry and sensitive skin, barrier damage is present a priori. Epidermal intercellular lipids become obviously defective or are formed in an inadequate amount or composition. The consequence is increased permeability of the horny layer and inadequate protection of the skin against loss of hygroscopic substances and water.

The barrier effect of the skin can be quantified via the determination of the transepidermal water loss (TEWL). This is the evaporation of water from inside the body without taking into account the loss of water during perspiration. Determination of the TEWL value has proven to be extraordinarily informative and can be used to diagnose chapped or cracked skin, for determining the compatibility of surfactants which have very different chemical structures, and more besides.

For the beauty and well cared-for appearance of the skin, the proportion of water in the uppermost layer of the skin is of greatest significance. It can be favorably influenced within a limited scope by introducing moisture regulators.

Anionic surfactants, which are generally constituents of cleansing preparations, can lastingly increase the pH in the horny layer, which severely hinders regenerative processes which serve to restore and renew the barrier function of the skin. In this case, a new, frequently very unfavorable state of equilibrium is established in the horny layer between regeneration and the loss of essential substances as a result of regular extraction; this state has a decisive adverse effect on the outer appearance of the skin and the physiological mode of function of the horny layer.

For the purposes of the present invention, skin care is understood primarily as meaning that the natural function of the skin as a barrier against environmental influences (e.g. dirt, chemicals, microorganisms) and against the loss of substances endogenous to the body (e.g. water, lipids, electrolytes) is strengthened or restored.

Products for the care, treatment and cleansing of dry and stressed skin are known per se. However, their contribution to the regeneration of a physiologically intact, hydrated and smooth horny layer is limited with regard to extent and time.

The effect of ointments and creams on the barrier function and the hydration of the horny layer is based essentially on the coverage (occlusion) of the areas of skin treated. The ointment or cream represents, as it were, a (second) artificial barrier which is intended to prevent loss of water by the skin.

It is equally easy to remove this physical barrier, for example using cleansers, again, as a result of which the original, impaired state is again achieved. Moreover, the skin care effect can decrease upon regular treatment. After use of the product is stopped, the skin reverts very quickly to the state prior to the start of treatment. In the case of certain products, the condition of the skin is even temporarily worsened in some circumstances. A permanent product effect is therefore generally not achieved or achieved only to a limited extent.

The effect of some pharmaceutical preparations on the barrier function of the skin consists even in selected damage to the barrier, which is intended to permit active ingredients to be able to penetrate into or through the skin into the body. Here, a disturbed appearance of the skin as a side effect is accepted to some extent as a small price to pay.

The effect of caring cleansing products consists essentially in an efficient refatting with sebum lipid-like substances. The simultaneous reduction in the surfactant content of such preparations permits a further limitation of the damage to the horny layer barrier.

However, the prior art lacks preparations which have a positive effect on the barrier function and hydration of the horny layer and enhance or even restore the physicochemical properties of the horny layer and, in particular, of the lamellae comprising intercellular lipids.

The object of the present invention was therefore to overcome the disadvantages of the prior art. In particular, skin care preparations and preparations for cleansing the skin were to be made available which retain or restore the barrier properties of the skin, particularly when the natural regeneration of the skin is inadequate. They should also be suitable for the treatment and prophylaxis of secondary damage of the drying-out of skin, for example fissures or inflammatory or allergic processes, or also of neurodermatitis. It was also an object of the present invention to provide stable skin care cosmetic and/or dermatological compositions which protect the skin against environmental influences such as sun and wind. In particular, the effect of the preparations was to be physiological, rapid and long-lasting.

Surprisingly, and in a manner which could not have been foreseen by the person skilled in the art, these objects are achieved by
cosmetic and dermatological preparations having an effective content of bile acids, their salts and/or their derivatives, it being possible for said active ingredients to be present either individually or as a mixture.

For the purposes of the present invention, "barrier strengthening" or "strengthening of the barrier function of the skin" is, in particular, to be understood as meaning the following effect: the active ingredients according to the invention interact with the lipids of the horny layer in a manner such that the arrangement of these lipids in the horny layer on a molecular plane is improved. This leads to the natural function of the skin as a barrier against environmental influences and against the loss of substances endogenous to the body being strengthened or restored.

In every respect the preparations according to the invention are extremely satisfactory preparations. It had been unforeseen for the person skilled in the art that the preparations according to the invention
better retain or restore the barrier properties of the skin,
better counteract drying-out of the skin,
better counteract skin aging and
better protect the skin against environmental influences than the prior art preparations.

Bile is the exocrine secretion of the liver whose main constituents are water (86.7%), bile acids (9.1%), bile pigments (3%), cholesterol (0.3%), and fatty acids, proteins and inorganic substances. The function of the bile liquid within the framework of fat digestion consists in the emulsification of water-insoluble constituents of food in the intestine and in the conversion of water-insoluble compounds to resorbable choleic acids. In addition, the bile acids, which occur in the bile as salts, keep the cholesterol in solution and facilitate its elimination. Bile acids are primarily substituted cholanic acids conjugated with glycine (glycocholic acid) or taurine (taurocholic acid), which have the following structural formula:

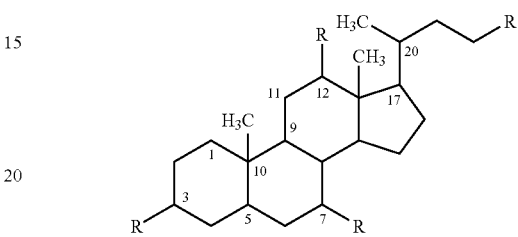

Advantageous for the purposes of the present invention are, for example, dehydrocholic acid, which is characterized by the following structure, and its salts:

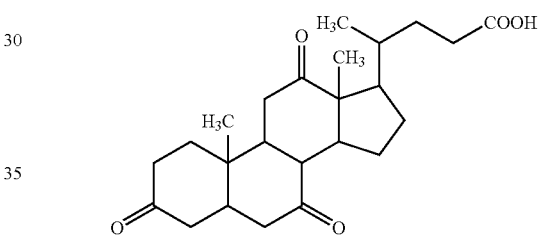

Also advantageous are lithocholic acid, which is characterized by the following structure, and its salts:

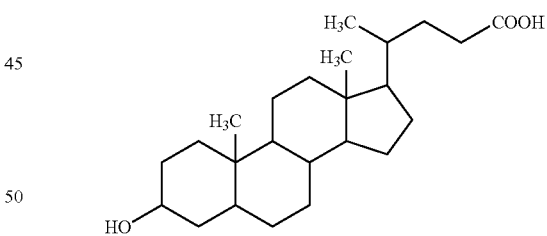

Also advantageous are cholic acid, which is characterized by the following structure, and its salts:

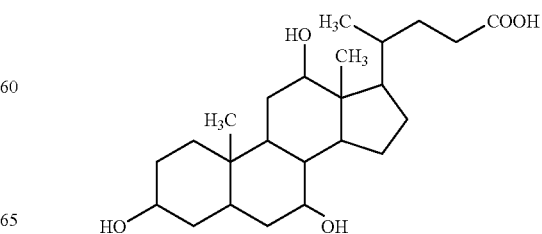

Also advantageous are glycocholic acid, which is characterized by the following structure, and its salts:

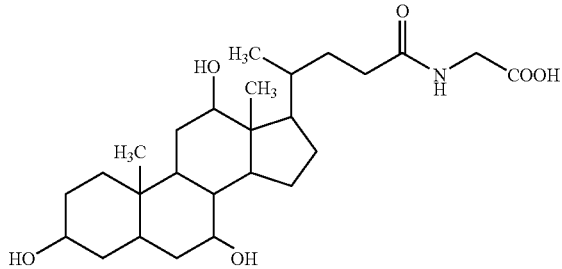

Also advantageous are taurolithocholic acid, which is characterized by the following structure, and its salts, in particular its sodium salt:

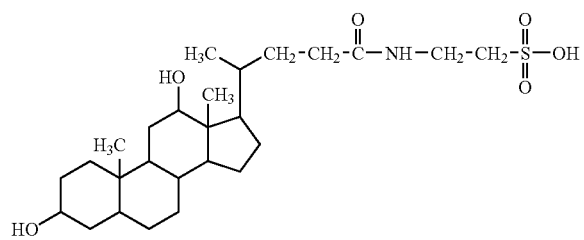

Particularly preferred for the purposes of the present invention are deoxycholic acid, which is characterized by the following structure, and its salts:

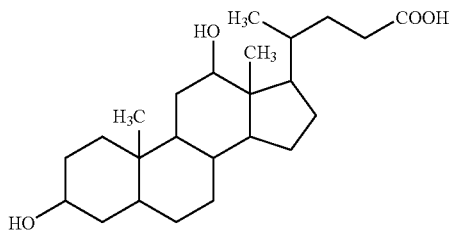

Also particularly preferred are ursodeoxycholic acid (chenodeoxycholic acid), which is characterized by the following structure, and its salts:

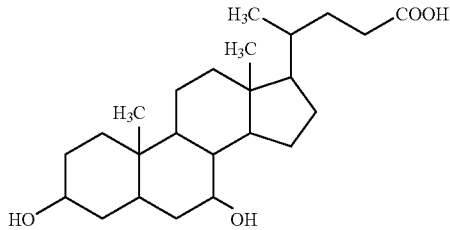

Also particularly preferred are taurocholic acid, which is characterized by the following structure, and its salts, in particular its sodium salt:

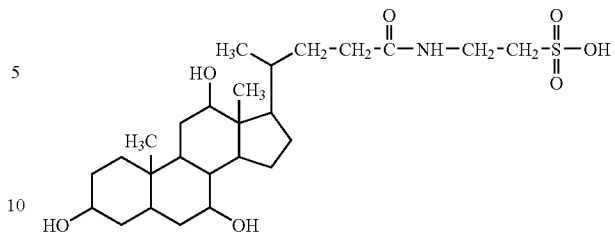

Also advantageous for the purposes of the present invention are the esters and ethers of the bile acids, in particular the esters and ethers of the aforementioned bile acids.

Bile acid ethers are obtainable by an etherification of at least one of the alcohol functions in position 3, 7 or 12 of the cholane ring. Particular preference is given to bile acid ethers obtainable by etherification of the alcohol function in position 3.

Advantageous for the purposes of the present invention are bile acid ethers obtainable by etherification with ethylene oxide, saturated and/or unsaturated, branched and/or unbranched alcohols having a chain length of from 2 to 22 carbon atoms.

Bile acid esters are obtainable by etherification of at least one of the alcohol functions in position 3, 7 or 12 of the cholane ring, and by esterification of the terminal acid functions. Advantageous for the purposes of the present invention are bile acid esters obtainable by esterification with saturated and/or unsaturated, branched and/or unbranched acids having a chain length of from 2 to 22 carbon atoms.

Also advantageous are bile acid esters obtainable by esterification of the terminal acid function with ethylene oxide, saturated and/or unsaturated, branched and/or unbranched alcohols having a chain length of from 2 to 22 carbon atoms.

Also advantageous for the purposes of the present invention are, in particular, the salts of the bile acids, in particular the alkali metal and/or alkaline earth metal salts, and the salts of mono- or divalent cations of elements from the transition groups, and also the lanthanides and/or actinides. Also advantageous are bile acid salts of ammonium (—NH$_3$), alkanolammonium derivatives having 2 to 9 carbon atoms in total, alkyl- or alkenyl-ammonium derivatives having 1 to 22 carbon atoms in total, pyridine, which may be substituted by an alkyl or alkenyl group which has 1 to 18 carbon atoms, and basic amino acids. According to the invention, particular preference is given to the sodium, potassium and/or triethanolamine salts of the bile acids.

The cosmetic or dermatological preparations or formulations according to the invention can have the customary composition and be used for the treatment, care and cleansing of the skin and/or of the hair and as a make-up product in decorative cosmetics. Accordingly, depending on their formulation, they may be used, for example, as skin protection cream, cleansing milk, sunscreen lotion, nourishing cream, day cream or night cream etc. It is optionally possible and advantageous to use the preparations according to the invention as a base for pharmaceutical formulations. The preparations according to the invention comprise, for example, 0.001 to 10% by weight, preferably 0.01% by weight to 1%, but in particular 0.01% by weight to 0.5% by weight, in each case based on the total weight of the preparations of the active ingredients according to the invention.

Also favorable are those cosmetic and dermatological preparations which are in the form of a sunscreen. In addition to one or more active ingredients according to the invention, these preferably comprise at least one UV-A filter substance and/or at least one UV-B filter substance and/or at least one inorganic pigment.

It is, however, also advantageous for the purposes of the present invention to provide cosmetic and dermatological preparations whose main purpose is not protection against sunlight, but which nevertheless comprise a content of UV protection substances. Thus, UV-A and UV-B filter substances are commonly incorporated into day creams, for example.

The cosmetic and dermatological preparations according to the invention may comprise cosmetic auxiliaries as are customarily used in such preparations, e.g. preservatives, bactericides, perfumes, antifoams, dyes, pigments which have a coloring action, thickeners, surface-active substances, emulsifiers, emollients, moisturizers and/or humectants, fats, oils, waxes and other customary constituents of a cosmetic or dermatological formulation, such as alcohols, polyols, polymers, foam stabilizers, electrolytes, organic solvents or silicone derivatives.

Depending on the type of product in each case, the amounts of cosmetic, dermatological or medicinal carrier substances and perfume to be used in each case can be readily determined by the person skilled in the art by simple exploratory experiments.

Preparations for the treatment and care of the skin are particularly preferred.

For use, the cosmetic and dermatological preparations according to the invention are applied to the skin and/or the hair in a sufficient amount in the manner customary for cosmetics.

Cosmetic and dermatological preparations according to the invention may exist in a variety of forms. Thus, for example, they may be a solution, an anhydrous preparation, an emulsion or microemulsion of the water-in-oil (W/O) type or of the oil-in-water (O/W) type, a multiple emulsion, for example of the water-in-oil-in-water (W/O/W) type, a gel, a solid stick, an ointment or also an aerosol. It is also advantageous to administer the active ingredients according to the invention in encapsulated form, e.g. in collagen matrices and other customary encapsulation materials, e.g. as cellulose encapsulations, in gelatin, wax matrices or liposomally encapsulated.

It is also possible and advantageous for the purposes of the present invention to incorporate the active ingredients according to the invention into aqueous systems or surfactant preparations for cleansing the skin and the hair.

In particular, the cosmetic and dermatological preparations according to the invention may also comprise antioxidants. According to the invention, favorable antioxidants which may be used are all the antioxidants which are suitable or customary for cosmetic and/or dermatological uses.

The antioxidants are advantageously chosen from the group consisting of amino acids (for example glycine, histidine, tyrosine, tryptophan) and derivatives thereof, imidazoles (for example urocanic acid) and derivatives thereof, peptides such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (for example buthionine sulfoximines, homocysteine sulfoximine, buthionine sulfones, penta-, hexa- and hepta-thionine sulfoximine) in very low tolerated doses (for example pmol to µmol/kg), and furthermore (metal) chelating agents (for example α-hydroxy-fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (for example ZnO, ZnSO$_4$), selenium and derivatives thereof (for example selenomethionine), stilbenes and derivatives thereof (for example stilbene oxide, trans-stilbene oxide) and the derivatives of these active ingredients mentioned which are suitable according to the invention (salts, esters, ethers, sugars, nucleotides, nucleosides, peptides and lipids).

The amount of the abovementioned antioxidants (one or more compounds) in the preparations according to the invention is preferably from 0.001 to 30% by weight, particularly preferably 0.05–20% by weight, in particular 1–10% by weight, based on the total weight of the preparation.

If vitamin E and/or derivatives thereof is or are the antioxidant or antioxidants, it is advantageous to choose the respective concentrations thereof from the range 0.001–10% by weight, based on the total weight of the formulation.

If vitamin A or vitamin A derivatives or carotenes or derivatives thereof is or are the antioxidant or antioxidants, it is advantageous to choose the respective concentrations thereof from the range 0.001–10% by weight, based on the total weight of the formulation.

The examples below serve to illustrate the present invention without limiting it. The numerical values in the examples are percentages by weight, based on the total weight of the respective preparations.

| Example formulations: | % by wt. |
|---|---|
| 1. Lecithin fluid | |
| Lecithin | 5.00 |
| Ursodeoxycholic acid | 0.50 |
| Cetearyl alcohol | 1.00 |
| Glycerol | 3.00 |

-continued

| Example formulations: | % by wt. |
|---|---|
| Antioxidants, preservatives, neutralizing agents, perfume, dyes | q.s. |
| Water | ad 100 |
| 2. Hydrodispersion gel | |
| Stearyl alcohol | 2.00 |
| Behenyl alcohol | 2.00 |
| Ceramide 3 | 0.20 |
| Taurodeoxycholic acid | 0.10 |
| Carbopol | 0.30 |
| Hydroxyethylcellulose | 0.40 |
| Glycerol | 3.00 |
| Panthenol | 1.00 |
| Caprylic/capric triglyceride | 3.00 |
| Isopropyl palmitate | 3.00 |
| Shea butter | 2.00 |
| Antioxidants, preservatives, neutralizing agents, perfume, dyes, | q.s. |
| Water | ad 100 |
| 3. Light gel | |
| Sucrose stearate | 3.00 |
| Cetearyl alcohol | 2.00 |
| Deoxycholic acid | 0.02 |
| Carbopol | 0.50 |
| Glycerol | 3.00 |
| Antioxidants, preservatives, neutralizing agents, perfume, dyes | q.s. |
| Water | ad 100 |
| 4. O/W cream | |
| Sucrose stearate | 4.00 |
| Sucrose laurate | 2.00 |
| Taurolithocholic acid | 0.02 |
| Cetearyl alcohol | 3.00 |
| Glycerol | 3.00 |
| Dimethicone | 2.00 |
| Mineral oil | 5.00 |
| Isopropyl palmitate | 3.00 |
| Sunflower oil | 3.00 |
| Hydrogenated coconut fatty acid glyceride | 2.50 |
| Liquorice root extract | 2.00 |
| Carbomer | 0.20 |
| NaOH 45% strength | 0.10 |
| Antioxidants, preservatives, neutralizing agents, perfume, dyes | q.s. |
| Water | ad 100 |
| 5. O/W lotion | |
| Stearic acid | 1.50 |
| Sorbitan monostearate | 0.50 |
| Ursodeoxycholic acid | 0.05 |
| Myristyl alcohol | 1.00 |
| Glycerol monostearate | 0.50 |
| Paraffin oil, subliquidum | 10.00 |
| Dimethicone | 1.00 |
| Octyldodecanol | 2.00 |
| Hydrogenated coconut fatty acid glyceride | 0.50 |
| Carbomer | 0.10 |
| Serine | 0.50 |
| Glycerol | 5.00 |
| Tocopherol acetate | 0.50 |
| Antioxidants, preservatives, neutralizing agents, perfume, dyes | q.s. |
| Water | ad 100 |
| 6. W/O lotion | |
| PEG-7 hydrogenated castor oil | 4.00 |
| Glycocholic acid | 0.01 |
| Beeswax | 3.00 |
| Vaseline | 4.00 |
| Ozokerite | 4.00 |
| Paraffin oil, subliquidum | 10.00 |
| Glycerol | 5.00 |
| Octyl methoxycinnamate | 2.50 |
| Methylbenzylidenecamphor | 2.50 |
| Tocopherol acetate | 1.00 |
| Magnesium sulfate 7 $H_2O$ | 0.70 |
| Antioxidants, preservatives, neutralizing agents, perfume, dyes | q.s. |
| Water | ad 100 |

-continued

| Example formulations: | % by wt. |
|---|---|
| 7. W/O cream | |
| PEG-7 hydrogenated castor oil | 4.00 |
| Wool wax alcohol | 1.50 |
| Deoxycholic acid | 0.05 |
| Vaseline | 9.00 |
| Ozokerite | 4.00 |
| Paraffin oil, subliquidum | 10.00 |
| Urea | 10.00 |
| Magnesiumsulfate 7 $H_2O$ | 0.70 |
| Lactic acid | 0.30 |
| Sodium lactate | 2.50 |
| Antioxidants, preservatives, neutralizing agents, perfume, dyes | q.s. |
| Water | ad 100 |
| 8. Silicone emulsion | |
| Dimethicone copolyol | 2.00 |
| Cyclomethicone | 5.00 |
| Dimethicone | 3.0 |
| Paraffin oil, subliquidum | 8.00 |
| Wheatgerm oil | 4.0 |
| Dehydrocholic acid | 0.02 |
| Glycerol | 10.0 |
| Sodium chloride | 1.00 |
| Antioxidants, preservatives, neutralizing agents, perfume, dyes | q.s. |
| Water | ad 100 |
| 9. Ointment | |
| Vaseline | 36.00 |
| Ceresine | 10.00 |
| Zinc oxide | 4.00 |
| Wheatgerm oil | 20.00 |
| Taurocholic acid | 0.02 |
| Antioxidants, preservatives, neutralizing agents, perfume, dyes | q.s. |
| Paraffin oil | ad 100 |
| 10. Skin oil | |
| Cetyl palmitate | 3.00 |
| $C_{12-15}$ Alkyl benzoate | 2.00 |
| Polyisobutene | 10.00 |
| Squalane | 2.00 |
| Ursodeoxycholic acid | 0.05 |
| Antioxidants, preservatives, neutralizing agents, perfume, dyes | q.s. |
| Paraffin oil | ad 100 |
| 11. Bath oil | |
| Paraffin oil | 20.00 |
| PEG-40 hydrogenated castor oil | 5.00 |
| Deoxycholic acid | 0.50 |
| Antioxidants, preservatives, neutralizing agents, perfume, dyes | q.s. |
| Soybean oil | ad 100 |
| 12. Lip care stick | |
| Caprylic/capric triglyceride | 25.00 |
| Octyldodecanol | 25.00 |
| Ceramide 3 | 0.50 |
| Ursodeoxycholic acid | 0.20 |
| Beeswax | 20.00 |
| Cetyl palmitate | 8.00 |
| Jojoba oil | 5.00 |
| Carnauba wax | 4.00 |
| Tocopherol acetate | 0.75 |
| Antioxidants, preservatives, neutralizing agents, perfume, dyes | q.s. |
| Squalane | ad 100 |
| 13. Emulsion lip care stick | |
| Caprylic/capric triglyceride | 30.00 |
| Octyldodecanol | 20.00 |
| Polyglyceryl-3 dioleate | 3.50 |
| Beeswax | 10.00 |
| Dehydrocholic acid | 0.10 |
| $C_{20-40}$ Alkyl stearate | 5.00 |
| Jojoba oil | 5.00 |
| Carnauba wax | 2.00 |
| Tocopherol acetate | 0.75 |
| Water | 5.00 |

| Example formulations: | % by wt. |
|---|---|
| Antioxidants, preservatives, neutralizing agents, perfume, dyes | q.s. |
| Squalane | ad 100 |
| 14. Lipstick | |
| Caprylic/capric triglyceride | 22.00 |
| Octyldodecanol | 22.00 |
| Ursodeoxycholic acid | 0.20 |
| PEG-5 soya sterol | 0.50 |
| Beeswax hydrolysate | 5.00 |
| Beeswax | 15.00 |
| Cetyl palmitate | 2.00 |
| Jojoba oil | 5.00 |
| Carnauba wax | 2.00 |
| Tocopherol acetate | 0.75 |
| Color pigments, color lakes, titanium dioxide | q.s. |
| Antioxidants, preservatives, neutralizing agents, perfume, dyes | q.s. |
| Squalane | ad 100 |
| 15. Emulsion foundation | |
| Sorbitan monostearate | 1.50 |
| Sorbitan monooleate | 1.00 |
| Glycerol monostearate | 1.00 |
| Taurocholic acid | 0.20 |
| Glyceryl lanolate | 1.00 |
| Paraffin oil, subliquidum | 7.00 |
| Octyldodecanol | 7.00 |
| Hydrogenated coconut fatty acid glyceride | 4.00 |
| Octyl methoxycinnamate | 2.00 |
| Butylmethoxydibenzoylmethane | 1.00 |
| Carbomer | 0.10 |
| Glycerol | 5.00 |
| 1,3-Butylene glycol | 2.00 |
| Tocopherol acetate | 1.00 |
| Sodium octenyl succinate starch (Amiogum ® from American Maize-Products Company/CERSTAR) | 2.50 |
| Magnesium silicate | 1.00 |
| Mica | 1.00 |
| Iron oxide | 1.00 |
| Titanium dioxide | 2.50 |
| Talc | 5.00 |
| Antioxidants, preservatives, neutralizing agents, perfume, dyes | q.s. |
| Water | ad 100 |
| 16. Haircare composition | |
| TEA - Cocoyl hydrolyzed collagen | 30.00 |
| Monoethanolamine lauryl sulfate | 25.00 |
| Almond oil | 2.00 |
| PEG-25 soya sterol | 2.00 |
| Deoxycholic acid | 0.20 |
| Sodium chloride | 1.00 |
| Antioxidants, preservatives, neutralizing agents, perfume, dyes | q.s. |
| Water | ad 100 |
| 17. Care shampoo | |
| Sodium lauryl sulfate | 34.00 |
| Disodium lauryl sulfosuccinate | 6.00 |
| Cocoamidopropylbetaine | 10.00 |
| Lithocholic acid | 0.02 |
| Glycol distearate | 5.00 |
| Antioxidants, preservatives, neutralizing agents, perfume, dyes | q.s. |
| Water | ad 100 |
| 18. Pump spray | |
| PEG-40 hydrogenated castor oil | 2.00 |
| Glycerol | 1.00 |
| PEG-25 soja sterol | 2.00 |
| Glycocholic acid | 0.02 |
| Antioxidants, preservatives, neutralizing agents, perfume, dyes | q.s. |
| Water | ad 100 |
| 19. Roll-on emulsion | |
| Triceteareth phosphate | 0.30 |
| Octyldodecanol | 2.00 |
| $C_{12-15}$ Alkyl benzoate | 2.00 |
| $C_{10-30}$ Alkyl acrylate | 0.15 |
| Taurolithocholic acid | 0.05 |
| Antioxidants, preservatives, neutralizing agents, perfume, dyes | q.s. |
| Water | ad 100 |

The invention claimed is:

1. A cosmetic and/or dermatological preparation comprising a bile acid or salt thereof in an amount of about 0.01% to about 0.5% by weight, based on the total weight of the preparation, wherein the salt is selected from the group consisting of alkali metal and alkaline earth metal salts, salts of mono- or divalent cations of elements from the transition groups, salts of mono- or divalent cations of elements from the lanthanides, salts of mono or divalent cations of elements from the actinides, salts of ammonium (—NH3), and salts of basic amino acids, wherein said bile acid is selected from the group consisting of dehydrocholic acid, lithocholic acid, cholic acid, glycocholic acid, taurolithocholic acid, ursodeoxycholic acid and taurocholic acid wherein the bile acid or salt thereof is in an encapsulated form selected from the group consisting of collagen matrices, cellulose encapsulations, gelatin, wax matrices, and liposomal encapsulations.

2. The preparation according to claim 1, further comprising cosmetic or dermatological auxiliaries, selected from the group consisting of antioxidants, UV-A or UV-B filter compounds, inorganic pigments, and mixtures thereof.

3. The preparation according to claim 1, wherein the encapsulated form is in the form of a solution.

4. A method for strengthening the barrier function of the skin that comprises applying a barrier strengthening effective amount of a preparation of claim 1 to the skin.

5. The preparation of claim 1, further comprising antioxidants in an amount of 1–10% by weight, based on the total weight of the preparation.

6. The preparation of claim 1, further comprising vitamin E and/or derivatives thereof in an amount of 0.001–10% by weight, based on the total weight of the preparation.

7. The preparation of claim 6, wherein said vitamin E and/or derivatives thereof is tocopheryl acetate.

* * * * *